US010301265B2

(12) United States Patent
Roxas-Duncan et al.

(10) Patent No.: US 10,301,265 B2
(45) Date of Patent: May 28, 2019

(54) SMALL MOLECULE INHIBITORS OF BOTULINUM NEUROTOXINS

(76) Inventors: Virginia I. Roxas-Duncan, Fort Detrick, MD (US); Leonard A. Smith, Fort Detrick, MD (US); Nizamettin Gul, Fort Detrick, MD (US); John H. Cardellina, II, Fort Detrick, MD (US); Rebecca C. Vieira, Fort Detrick, MD (US); Susan M. Ensel, Fort Detrick, MD (US); David C. H. Yang, Washington, DC (US); Istvan J. Enyedy, Washington, DC (US); Sivanesan Dakshanamurthy, Washington, DC (US); Salimuddin Shah, Washington, DC (US)

( * ) Notice: Subject to any disclaimer, the term of this patent is extended or adjusted under 35 U.S.C. 154(b) by 0 days.

(21) Appl. No.: 13/058,764

(22) PCT Filed: May 28, 2009

(86) PCT No.: PCT/US2009/045546
§ 371 (c)(1),
(2), (4) Date: Aug. 22, 2011

(87) PCT Pub. No.: WO2009/151972
PCT Pub. Date: Dec. 17, 2009

(65) Prior Publication Data
US 2011/0294848 A1    Dec. 1, 2011

Related U.S. Application Data

(60) Provisional application No. 61/056,664, filed on May 28, 2008.

(51) Int. Cl.
*C07D 215/26* (2006.01)
*C07D 215/40* (2006.01)
*C07D 401/12* (2006.01)

(52) U.S. Cl.
CPC ......... *C07D 215/26* (2013.01); *C07D 215/40* (2013.01); *C07D 401/12* (2013.01)

(58) Field of Classification Search
CPC ... C07D 215/26; C07D 215/40; C07D 401/12
See application file for complete search history.

(56) References Cited

U.S. PATENT DOCUMENTS 5,958,970 A * 9/1999 Hua et al. ............... 514/455
2007/0086979 A1* 4/2007 Chevrier et al. ......... 424/85.1

FOREIGN PATENT DOCUMENTS

WO    WO 2008014602 A1 *  2/2008
WO    WO 2011/022721      2/2011

OTHER PUBLICATIONS

Miyano et al. "Nucleophilic Addition to Schiff Base. II Addition of Phenols to N-(2-Pyridylmethylene)anilines" Chem. Pharm. Bull., 1971, vol. 19, No. 6, pp. 1131-1136.*
Patel et al. "Synthesis, Characterization and Glass Reinforcement of Poly(Urea-imide)s, Part-1" International Journal of Polymeric Materials, 1998, vol. 40, pp. 115-126.*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Sheridan R.P. "The Most Common Chemical Replacements in Drug-Like Compounds" J. Chem. Inf. Compu. Sci., 2002, vol. 42, pp. 103-108.*
Lu et al. "Discovery of a Nanomolar Inhibitor of the Human Murine Double Minute 2 (MDM2)-p53 Interaction through an Integrated, Virual Database Screening Strategy" J. med. Chem., 2006, vol. 49, pp. 3759-3762.*
Gould, P.L. International Journal of Pharmaceutics, 1986, vol. 33, pp. 201-217.*
Berkson et al. "Pilot screening programme for small molecule activators of p53" Int. J. Cancer, 2005, vol. 115, pp. 701-710.*
PubChem Bioassay (printed Mar. 23, 2015; test conducted on Jan. 8, 2008).*
Lu et al. "Discovery of a Nanomolar Inhibitor of the Human Murine Double Minute 2 (MDM2)—p53 Interaction through an Integrated, Virtual Database Screening Strategy", J. Med. Chem., 2006, vol. 49, pp. 3759-3762. (Year: 2006).*
Burnett, et al (2003) Novel small-molecule inhibitors of botulinum neurotoxin A metalloprotease activity. Biochem. Biophys. Res. Commun. 310:84-93.
Sheridan, et al. (1997) Structural features of aminoquinolines necessary for antagonist activity against botulinum neurotoxin. Toxicon 35:1439-1451.

* cited by examiner

*Primary Examiner* — Kendra D Carter
(74) *Attorney, Agent, or Firm* — Nash and Titus, LLC

(57) ABSTRACT

The invention provides potent quinolinol-based BoNT/A small-molecule inhibitors of botulinum neurotoxins, in particular of *Clostridium botulinum* serotype A neurotoxins. The invention also provides methods of using these small-molecule inhibitors to inhibit infections by *Clostridium botulinum*, as well as, methods of preventing infections by *Clostridium botulinum* through materials that may be ingested.

6 Claims, 4 Drawing Sheets

Specification includes a Sequence Listing.

```
BoNT/A LC Crystal Structure
            │
            ▼
NCI Database ──── 3D model of binding pocket
            │
            │ Virtual Screening (DOCK)
            ▼
      500 candidates
            │ Narrow down candidates (scores,
            │ structures, best fit in binding site)
            ▼
        100 hits
            │ Enzymatic Assay (HPLC)
            ▼
       7 compounds
            │ Scale down (select top compound)
            ▼
        1 compound
            │ Similarity Search
            ▼
        55 analogs
            │ HPLC-based Assays
            ▼
        5 analogs
            │ Cell Culture Assay
            ▼
        5 analogs
            │ MPNHDA
            ▼
        5 analogs
            │
            ▼
       Final Results
```

FIG. 1

SEQUENCE LISTING

<160> NUMBER OF SEQ ID NOS: 8

<210> SEQ ID NO 1
<211> LENGTH: 7

```
<212> TYPE: PRT
<213> ORGANISM: Artificial Sequence
<220> FEATURE:
<223> OTHER INFORMATION: peptide inhibitor of Clostridium botulism
      neurotoxin serotype A commercially available from EMD Chemicals
      Inc.
<220> FEATURE:
<221> NAME/KEY: MISC_FEATURE
<223> OTHER INFORMATION: The n-terminal contains a variable acetyl
      sequence
<220> FEATURE:
<221> NAME/KEY: MISC_FEATURE
<223> OTHER INFORMATION: The c-terminal contains an amino group

<400> SEQUENCE: 1

Cys Arg Ala Thr Lys Met Leu
1               5

<210> SEQ ID NO 2
<211> LENGTH: 17
<212> TYPE: PRT
<213> ORGANISM: Homo sapiens
<220> FEATURE:
<221> NAME/KEY: MISC_FEATURE
<223> OTHER INFORMATION: The n-terminal contains a variable acetyl
      sequence
<220> FEATURE:
<221> NAME/KEY: MISC_FEATURE
<223> OTHER INFORMATION: The c-terminal contains an amino group

<400> SEQUENCE: 2

Ser Asn Lys Thr Arg Ile Asp Glu Ala Asn Gln Arg Ala Thr Lys Met
1               5                   10                  15

Leu

<210> SEQ ID NO 3
<211> LENGTH: 35
<212> TYPE: PRT
<213> ORGANISM: Homo sapiens
<220> FEATURE:
<221> NAME/KEY: MISC_FEATURE
<223> OTHER INFORMATION: The n-terminal contains a variable acetyl
      sequence
<220> FEATURE:
<221> NAME/KEY: MISC_FEATURE
<223> OTHER INFORMATION: The c-terminal contains an amino group

<400> SEQUENCE: 3

Leu Ser Glu Leu Asp Asp Arg Ala Asp Ala Leu Gln Ala Gly Ala Ser
1               5                   10                  15

Gln Phe Glu Thr Ser Ala Ala Lys Leu Lys Arg Lys Tyr Trp Trp Lys
            20                  25                  30

Asn Leu Lys
        35

<210> SEQ ID NO 4
<211> LENGTH: 5
<212> TYPE: PRT
<213> ORGANISM: Clostridium botulinum
<220> FEATURE:
<221> NAME/KEY: misc_feature
<222> LOCATION: (3)..(4)
<223> OTHER INFORMATION: Xaa can be any naturally occurring amino acid

<400> SEQUENCE: 4

His Glu Xaa Xaa His
1               5
```

```
<210> SEQ ID NO 5
<211> LENGTH: 1275
<212> TYPE: DNA
<213> ORGANISM: Clostridium botulinum
<220> FEATURE:
<221> NAME/KEY: misc_feature
<223> OTHER INFORMATION: The n-terminal contains a variable acetyl
      sequence
<220> FEATURE:
<221> NAME/KEY: misc_feature
<223> OTHER INFORMATION: The c-terminal contains an amino group

<400> SEQUENCE: 5
atgcagttcg ttaacaaaca gttcaactac aaagacccgg ttaacggtgt tgacatcgct    60
tacatcaaaa tcccgaacgt tggtcagatg cagccggtta agcattcaa atccacaac    120 aaaatctggg ttatcccgga acgtgacact ttcactaacc cggaagaagg tgacctgaac    180
ccgccgccgg aagctaaaca ggttccggtt tcttactacg actctactta cctgtctact    240
gacaacgaaa aggacaacta cctgaaaggt gttactaaac tgtttgaacg tatctactct    300
actgacctgg gtcgcatgct gctcacttct atcgttcgtg gtatcccgtt ctggggtggt    360
tctactatcg acactgaact gaaagttatc gacactaact gcatcaacgt tatccagccg    420
gacggttctt accgttctga agaactgaac ctggttatca tcggtccgtc tgctgacatc    480
atccagtttg aatgcaaatc tttcggtcac gaagttctga acctgactcg taacggttac    540
ggttctactc agtacatccg tttctctccg gacttcactt tcggtttcga agaatctctg    600
gaagttgaca ctaacccgct gctgggtgct ggtaaattcg ctactgaccc ggctgttact    660
ctggctcacg aactgatcca cgctggtcac cgtctgtacg gtatcgctat caaccccgaac    720 cgtgttttca agttaacac taacgcttac tacgaaatgt ctggtctgga gtttcttttt    780
gaagaactgc gtactttcgg tggtcacgac gctaaattca tcgactctct gcaggaaaac    840
gagttccgtc tgtactacta caacaaattc aaagacatcg cttctactct gaacaaagct    900
aaatctatcg ttggtaccac tgcttctctg cagtacatga gaacgttttt caaagaaaag    960
tacctgctgt ctgaagacac ttctggtaaa ttctctgttg acaaactgaa attcgacaaa   1020
ctgtacaaaa tgctgactga atctacact gaagacaact tcgttaaatt cttcaaagtt   1080
ctgaaccgta aaacttacct gaacttcgac aaagctgttt tcaaaatcaa catcgttccg   1140
aaagttaact acactatcta cgacggtttc aacctgcgta acactaacct ggctgctaac   1200
ttcaacggtc agaacactga atcaacaac atgaacttca ctaaactgaa gaacttcact   1260
ggtctgtttg agttc                                                   1275

<210> SEQ ID NO 6
<211> LENGTH: 425
<212> TYPE: PRT
<213> ORGANISM: Clostridium botulinum

<400> SEQUENCE: 6

Met Gln Phe Val Asn Lys Gln Phe Asn Tyr Lys Asp Pro Val Asn Gly
1               5                   10                  15

Val Asp Ile Ala Tyr Ile Lys Ile Pro Asn Val Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
```

| | | | | 65 | | | | 70 | | | | 75 | | | | 80 | |
|---|---|---|---|---|---|---|---|---|---|---|---|---|---|---|---|---|---|

Asp Asn Glu Lys Asp Asn Tyr Leu Lys Gly Val Thr Lys Leu Phe Glu
              85                    90                    95

Arg Ile Tyr Ser Thr Asp Leu Gly Arg Met Leu Leu Thr Ser Ile Val
            100                  105                110

Arg Gly Ile Pro Phe Trp Gly Gly Ser Thr Ile Asp Thr Glu Leu Lys
            115                  120                125

Val Ile Asp Thr Asn Cys Ile Asn Val Ile Gln Pro Asp Gly Ser Tyr
130                    135                  140

Arg Ser Glu Glu Leu Asn Leu Val Ile Gly Pro Ser Ala Asp Ile
145                  150                155                160

Ile Gln Phe Glu Cys Lys Ser Phe Gly His Glu Val Leu Asn Leu Thr
            165                  170                175

Arg Asn Gly Tyr Gly Ser Thr Gln Tyr Ile Arg Phe Ser Pro Asp Phe
            180                  185                190

Thr Phe Gly Phe Glu Glu Ser Leu Glu Val Asp Thr Asn Pro Leu Leu
            195                  200                205

Gly Ala Gly Lys Phe Ala Thr Asp Pro Ala Val Thr Leu Ala His Glu
            210                  215                220

Leu Ile His Ala Gly His Arg Leu Tyr Gly Ile Ala Ile Asn Pro Asn
225                  230                235                240

Arg Val Phe Lys Val Asn Thr Asn Ala Tyr Tyr Glu Met Ser Gly Leu
            245                  250                255

Glu Val Ser Phe Glu Glu Leu Arg Thr Phe Gly Gly His Asp Ala Lys
            260                  265                270

Phe Ile Asp Ser Leu Gln Glu Asn Glu Phe Arg Leu Tyr Tyr Tyr Asn
            275                  280                285

Lys Phe Lys Asp Ile Ala Ser Thr Leu Asn Lys Ala Lys Ser Ile Val
            290                  295                300

Gly Thr Thr Ala Ser Leu Gln Tyr Met Lys Asn Val Phe Lys Glu Lys
305                  310                315                320

Tyr Leu Leu Ser Glu Asp Thr Ser Gly Lys Phe Ser Val Asp Lys Leu
            325                  330                335

Lys Phe Asp Lys Leu Tyr Lys Met Leu Thr Glu Ile Tyr Thr Glu Asp
            340                  345                350

Asn Phe Val Lys Phe Phe Lys Val Leu Asn Arg Lys Thr Tyr Leu Asn
            355                  360                365

Phe Asp Lys Ala Val Phe Lys Ile Asn Ile Val Pro Lys Val Asn Tyr
370                  375                380

Thr Ile Tyr Asp Gly Phe Asn Leu Arg Asn Thr Asn Leu Ala Ala Asn
385                  390                395                400

Phe Asn Gly Gln Asn Thr Glu Ile Asn Asn Met Asn Phe Thr Lys Leu
            405                  410                415

Lys Asn Phe Thr Gly Leu Phe Glu Phe
            420                  425

<210> SEQ ID NO 7
<211> LENGTH: 1293
<212> TYPE: DNA
<213> ORGANISM: Clostridium botulinum

<400> SEQUENCE: 7

```
atgccgaaaa tcaactcgtt caactacaac gacccggtga atgaccgcac aatcctgtac      60
attaagccgg gcggttgcca ggagttctac aagagcttta acattatgaa gaacatctgg     120
```

```
atcatccctg aacgcaatgt gatcgggaca acgccacaag atttccaccc tccgacttcg    180
ctcaaaaacg gggactcctc ctactacgac ccaaattact tgcaaagcga tgaggagaaa    240
gatcggttcc tgaagattgt gacaaagatc ttcaaccgta ttaacaacaa tctctcgggg    300
ggcatcctcc tggaggaatt atccaaggcg aaccctta cc tgggcaacga caacactcca    360
gacaaccagt tccacattgg cgacgcctcc gcggtggaga tcaagttctc gaatggcagt    420
caggacatcc ttctccctaa tgtcattatt atgggcgccg agccggacct tttttgaaacc   480 aattccagca acatctcgct cgcaacaac  tacatgccga gcaatcacgg ctttgggtcg    540
atcgcgatcg tgactttctc gccggagtac tcctttcgct tcaacgacaa ctccatgaac    600
gagttcattc aggacccggc gctcaccctc atgcacgagc tgatccactc gttacatggc    660
ttgtacggcg cgaaggggat cacgaccaag tataccatta cgcagaaaca gaacccactt    720
atcacgaaca tccgtgggac gaacatcgag gagttcctca cgttcggggg gaccgacctg    780
aacattatca ccagcgccca gtccaacgac atttacacga acctgctggc agattacaaa    840
aaaattgcct ccaagctctc caaggtccag gtatcgaacc cgttgctcaa tccttacaag    900
gacgtcttcg aggctaagta tgggctggat aaggatgcct caggaatcta ctctgtgaac    960
atcaacaaat tcaacgacat cttcaagaag ctgtacagct tcaccgagtt tgacctcgcc    1020
accaagttcc aggtcaaatg tcggcaaacg tacattggcc agtataaata ttttaagctg    1080
tcgaatcttc tcaacgactc tatctataac atctccgagg ggtacaatat taacaactta    1140
aaagtcaact tccgagggca gaacgcaaat ctcaacccac ggattattac tcctattaca    1200
ggccgcgggc tcgtcaagaa gatcatccga ttttgcaaaa acattgtcag cgttaaaggc    1260
atccgtaagc tcgagcacca ccaccaccac cac                                 1293
```

<210> SEQ ID NO 8
<211> LENGTH: 431
<212> TYPE: PRT
<213> ORGANISM: Clostridium botulinum

<400> SEQUENCE: 8

```
Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140
```

```
Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Leu Glu His His His His His His
            420                 425                 430
```

SMALL MOLECULE INHIBITORS OF BOTULINUM NEUROTOXINS

RELATED APPLICATIONS

This application is a National Phase filing of PCT Patent Application No. PCT/US2009/045546, filed on May 28, 2009 which claims the priority benefit of Provisional Application Ser. 61/056,664, filed May 28, 2008. The teachings and content of these priority applications are hereby incorporated by reference in their entireties.

SEQUENCE LISTING

This application contains a sequence listing in paper format and in computer readable format, the teachings and content of which are incorporated by reference.

BACKGROUND OF THE INVENTION

Field of the Invention

The present invention relates to methods and compositions for inhibiting botulinum neurotoxins. Specifically, the invention provides quinolinol-based compositions and methods of using quinolinol-based compositions to inhibit the toxic effects of serotype A *Clostridium botulinum* neurotoxins.

Description of the Related Art

Botulinum neurotoxins (BoNTs), produced by the anaerobic, Gram-positive bacteria *Clostridium botulinum, C. baratii*, and *C. butyricum*, consist of seven immunologically distinct serotypes (types A-G). Botulinum neurotoxins are synthesized as ~150-kDa single-chain protoxins that are post-translationally processed by proteolytic cleavage to form a disulfide-linked dimer composed of a 100-kDa heavy chain (HC) and a 50-kDa light chain (LC) (27, 31, 35, 36). The HC comprises a 50-kDa C-terminal domain (Hc) that participates in the binding of toxin to productive ectoacceptors on the cell surface of peripheral cholinergic nerve cells (3). Toxin is taken up into the cell by receptor-mediated endocytosis (4) and the 50-kDa N-terminal domain (Hn) of the HC facilitates the translocation of the LC across an endosomal membrane into the cytosol of the nerve cell (30). The LC is a zinc-dependent endopeptidase that cleaves and inactivates SNARE (soluble N-ethylmaleimide-sensitive factor attachment protein receptor) proteins: SNAP-25, VAMP/synaptobrevin, and syntaxin (31, 36). SNARE proteins are essential for exocytosis of neurotransmitter, and cleavage of SNARE protein(s) by BoNT inhibits the release of acetylcholine from synaptic terminals leading to neuromuscular paralysis or botulism (31, 35).

Worldwide, about 1000 cases of human BoNT poisoning, predominantly caused by serotypes A and B, are reported yearly (17). In spite of advances in food production and storage/handling processes, cases of food-borne botulism persist, including a massive outbreak in Thailand (26) and the recent US botulism scare associated with canned chili and other products (2, 28).

Therapy for botulism consists of immunological intervention to neutralize and clear toxin from the circulation, and supportive care, which may include intubation and ventilatory assistance. However, while antibody therapy can be very effective, it has several limitations, including limited availability, lot-to-lot potency variability and short window of application. Clearly, there is a need for improved therapies and compounds.

Since small-molecules can be potentially used to treat pre- and post-exposure BoNT intoxication, research efforts to identify these antagonists have dramatically increased in recent years. However, the discovery and development of BoNT serotype A (BoNT/A) small-molecule inhibitors have long challenged researchers. Part of the difficulty in this endeavor can be attributed to the unusually large peptide substrate-enzyme interface (8) that requires a small-molecule with high affinity to effectively block substrate binding (47). Moreover, the BoNT toxin and its domains show considerable conformational flexibility, making design of effective inhibitors complicated. Despite these challenges, a number of papers have been published on the initial steps to discover and develop inhibitors of BoNT/A protease activity using different approaches. Using high throughput screening of the NCI Diversity Set, as well as a series of 4-aminoquinolines, Burnett et al. (11) identified several small-molecule inhibitors of BoNT/A, from which a common pharmacophore was predicted using molecular modeling (9). Similarly, a high throughput screen of a library of hydroxamates (6) resulted in the selection of 4-dichlorocinnamic hydroxamate as a lead structure for further development (5). Capkova et al. (12) structurally modified 2,4-dichlorocinnamic acid hydroxamate to improve its potency. On the other hand, a computational screen of 2.5 million compounds resulted in the identification of an inhibitor with a $K_i$ of 12 μM (32), but this value was later invalidated (47). Computer-aided optimization of this inhibitor resulted in an analog that showed a two-fold improvement in inhibitory potency and displayed competitive kinetics by chelating the active site zinc atom (47).

Though the above approaches have resulted in the identification of a number of small-molecule BoNT/A inhibitors, no compound has yet advanced to pre-clinical development. The majority of these leads have only been demonstrated to be effective in enzymatic assays (11, 12, 29, 32, 47). Only a few small-molecules have been tested in cell-based assays (5, 9, 15) that involved mixing the compound with the toxin, and not by pre-loading the inhibitor. To date, none of the recently-identified BoNT/A inhibitors has been tested in a tissue-based system, and to date only two compounds were reported to have minimal in vivo activity (15).

Herein, are provided the identification of potent quinolinol-based BoNT/A small-molecule inhibitors using an integrated strategy that combined in silico screening and successive biochemical tests, including enzymatic (HPLC-based), cell-based, and tissue-based assays.

SUMMARY OF THE INVENTION

The invention provides compositions for inhibiting botulinum neurotoxins, preferably a neurotoxin associated with *Clostridium botulinum* serotype A. The invention also provides methods of using these compositions to inhibit botulinum neurotoxins and of treating a subject exposed to botulinum neurotoxins.

Compositions of the invention comprise Formula 1, pharmaceutically acceptable salts of Formula 1, or combinations thereof. Formula 1 is wherein $R_1$, $R_2$, and $R_3$, being the same or different, are each selected from the group consisting of a H, a $C_1$ to $C_6$ straight or branched alkyl group, an aryl group, a halogen, $NR_5R_6$, $NO_2$, $CH_2OH$, $CHO$, $COOH$, $CN$, $SO_3H$, and $SO_2NR_7R_8$; wherein $R_5$, $R_6$, $R_7$, and $R_8$, being the same or different, are each selected from the group consisting of a H, a $C_1$ to $C_6$ straight or branched alkyl group, and an aryl group; wherein $R_4$ is selected from the group consisting of a straight or branched alkyl group and an aryl group; wherein $Ar_1$ is selected from the group consisting of a 5- and 6-membered aromatic and heteroaromatic rings and polycyclic aromatic and heteroaromatic ring systems; wherein X is selected from the group consisting of a O, $OCH_2$, S, $SCH_2$, $NR_9$, $NR_9CH_2$, $NR_9CO$, and $CH_2$; and wherein $R_9$ is selected from the group consisting of a H, a $C_1$ to $C_6$ straight or branched alkyl group, and an aryl group.

Claimed compositions of the invention exclude known compounds, for example the known compounds listed in Tables 1 and 2 herein are not claimed as compositions of the invention. Previously unknown analogs of the compounds listed in Tables 1 and 2 that inhibit botulinum neurotoxins are within the scope of the invention. Exemplary analogs are provided in Table 3. Preferably the compositions of the invention have little or no toxicity to a subject exposed to the compositions.

Suitable halogens for inclusion in the invention, alone or in combination, are chloro (Cl), fluoro (F), bromo (Br), and iodo (I).

Preferred aryl groups for inclusion in the invention, alone or in combination, are phenyl, pyridyl, thiophenyl, furyl, or indolyl rings.

An aspect of the invention is that compositions of the invention may include a pharmaceutically acceptable carrier, excipient, diluent, or adjuvant.

The invention also provides methods of using compositions comprising Formula 1, pharmaceutically acceptable salts of Formula 1, or combinations thereof. Specifically, the invention provides methods of inhibiting a botulinum neurotoxin in a subject by administering to the subject a composition comprising at least one compound, or pharmaceutically acceptable salt, of Formula 1. Compositions of the invention may be administered alone or as part of a therapy to treat botulism, i.e. an infection by C. botulinum.

In another aspect of the invention, the methods of the invention may be used to inhibit or prevent a C. botulinum infection, in particular a C. botulinum serotype A infection, by admixing one or more compositions of Formula 1, or a pharmaceutically acceptable salt thereof, with a substance suspected of including or being exposed to C. botulinum prior to such substance being ingested by a subject or such substance contacting another substance that is expected to be ingested by a subject.

In another aspect, compositions of the invention comprise Formula 2, pharmaceutically acceptable salts of Formula 2, or combinations thereof. Formula 2 is wherein X is O, S, Se, or NH; Y is CH or N; and $Ar_1$ is a monocyclic or bicyclic aromatic or heteroaromatic ring system, or a biphenyl or bipyridyl ring system, or a bridged biphenyl or bipyridyl ring system, any of which may be further substituted by one or more halogens (F, Cl, Br, I), $NR_1R_2$, $OR_3$, $SO_2NR_4R_5$, $SR_6$, $R_7$; and wherein $R_1$, $R_2$, $R_3$, $R_4$, $R_5$, $R_6$ and $R_7$, being the same or different, are each selected from the group consisting of H, a $C_1$ to $C_6$ straight or branched chain or cycloalkyl ring, a $C_1$ to $C_6$ straight or branched chain acyl group, or an aryl group.

In a further aspect methods of the invention include using compositions comprising Formula 2, pharmaceutically acceptable salts of Formula 2, or combinations thereof. Specifically, the invention provides methods of inhibiting a botulinum neurotoxin in a subject by administering to the subject a composition comprising at least one compound, or pharmaceutically acceptable salt, of Formula 2. Compositions of the invention may be administered alone or as part of a therapy to treat botulism, i.e. an infection by C. botulinum.

In another aspect of the invention, the methods of the invention may be used to inhibit or prevent a C. botulinum infection, in particular a C. botulinum serotype A infection, by admixing one or more compositions of Formula 2, or a pharmaceutically acceptable salt thereof, with a substance suspected of including or being exposed to C. botulinum prior to such substance being ingested by a subject or such substance contacting another substance that is expected to be ingested by a subject.

The invention also provides kits suitable for use with methods of the invention. Such kits include at least one composition of Formula 1, Formula 2, a pharmaceutically acceptable salt of either Formula 1 or Formula 2, or a combination thereof. Kits of the invention may also include instructions, a container for a composition of the invention, and components such as an adjuvant, diluent, pharmaceutically acceptable carrier and the like that may be admixed with a composition of the invention.

"Alkyl" alone or in combination means from 1 to 15, preferably 1 to 6, carbon atoms. Unless otherwise specified, an alkyl group is inclusive of a straight chain alkyl, branched alkyl, or cycloalkyl.

"Acyl" denotes groups —C(O)R, where R is hydrogen, lower alkyl, substituted lower alkyl, aryl, substituted aryl and the like.

"Aryl" refers to any functional group or substituent derived from a simple aromatic ring, may it be phenyl, pyridyl, furyl, thiopheneyl, indolyl, quinolinyl, etc. Simple aryl groups include phenyl, $C_6H_5$, which is derived from benzene, the tolyl group, $CH_3C_6H_4$, which is derived from toluene (methylbenzene), and the pyridyl group, $C_5H_4N$, which is derived from pyridine. Preferred aryl groups are simple aryl groups.

Herein, a "subject" is an animal or human. "Animal" refers to a fish, bird, or mammal, preferably the animal is a mammal such as a cat, dog, ungulate (e.g. horse, zebra, donkey, cattle/bison, rhinoceros, camel, hippopotamus, goat, swine, sheep, giraffe, okapi, moose, deer, tapir, antelope, or gazelle), rodent (e.g. mice, rats, and other small, gnawing mammals), bat, bear, primate, or cetacean.

Herein, "to inhibit or prevent a C. botulinum infection" means that one more symptoms associated with a C. botulinum infection is reduced by at least 10% in a subject as compared to a subject that receives no therapeutic treatment for a C. botulinum infection.

Unless defined otherwise, all technical and scientific terms used herein have the same meaning as is commonly understood by one of skill in the art to which this invention belongs at the time of filing. All patents and publications referred to herein are incorporated by reference herein.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Integrated experimental flow-chart to identify BoNT/A small-molecule inhibitors.

FIG. 2A. The reaction products were analyzed on SDS-PAGE gels. Lane 1, S25 alone; Lanes 2-7 contained S25+rELC; Lane 3, +NSC 84096; Lane 4, +CB 7967495; Lane 5, +CB 7969312; Lane 6, +NSC 84094; Lane 7, +CB 79698218. FIGS. 2B and 2C. Inhibition of BoNT/A-mediated SNAP-25 cleavage by small-molecules in cell-based assay. Efficacy of five small-molecule inhibitors at 15 mM (FIG. 2B) and at 10 mM (FIG. 2C) is shown: Lane 1 (With BoNT/A), Lane 2 (Without BoNT/A), Lanes 3-7 contained BoNT/A with inhibitor; Lane 3 (+NSC 84096), Lane 4 (+CB 7967495), Lane 5 (+CB 7969312), Lane 6 (+NSC 84094), Lane 7 (+CB 7968218). These blots represent three independent experiments.

DETAILED DESCRIPTION

Figure 2:
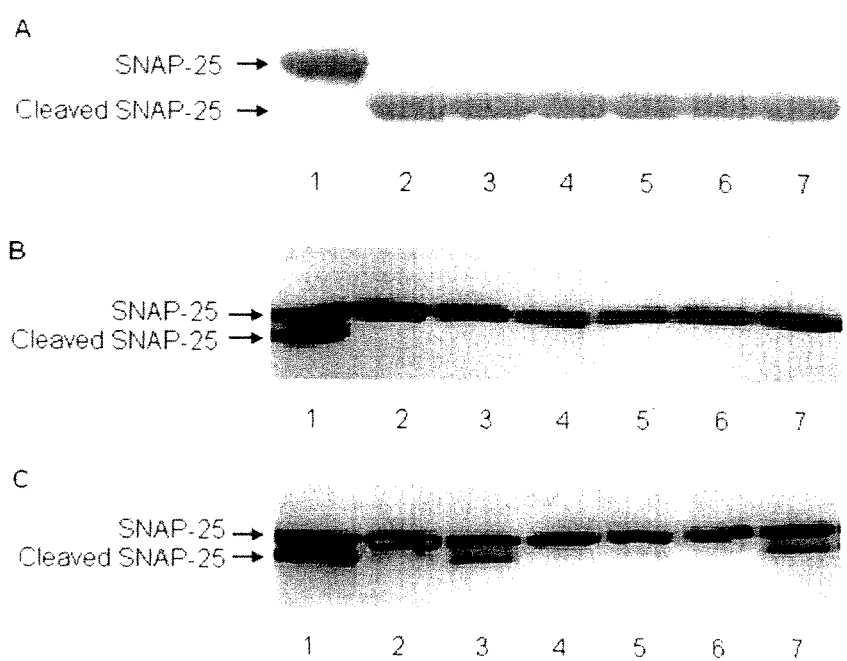
FIG. 2 shows the efficacy of small-molecules in inhibiting SNAP-25 cleavage.

The invention provides small-molecule inhibitors of *C. botulinum* neurotoxin serotype A (BoNT/A), as well as, methods of using these small molecule inhibitors to inhibit or treat botulism.

Eight small-molecule inhibitors of BoNT serotype A were initially identified by using in silico screening of the NCI database followed by HPLC protease assays (see Table 1). A substructure/similarity search was used to identify analogs of the lead hit NSC 1010 (see Table 2), and focus was placed on five of its most potent analogs, i.e., NSC 84094, NSC 84096, CB 7967495, CB 7968218 and CB 7969312 (see Table 3). Not only were these five analogs highly effective against the full-length BoNT/A LC in the HPLC-based assays, they were also very active against a truncated form (1-425) of BoNT/A LC. The extent of inhibition and the $IC_{50}$ values of these leads were comparable to or even better than those of previously reported small-molecule inhibitors (5, 6, 9-12, 15, 29, 32). No small-molecule is known to have been previously found to be active against both full-length and truncated forms of BoNT/A LC. Currently, it still remains unclear what form of light chain exists in the cytosol during the actual BoNT catalysis of SNARE proteins.

The crystal structures of the endopeptidase of different serotypes of BoNT are very similar. The HEXXH (SEQ ID NO: 4) motif that is characteristic of the catalytic site of Zn-endopeptidase is conserved. For instance, the active sites of BoNT/A and BoNT/B endopeptidases differ only in two residues: F162 and F193 in BoNT/A correspond to N169 and S200 in BoNT/B (32). Thus, it is conceivable for some BoNT/A inhibitors also to be active against other serotypes. Here, the five analogs exhibited cross reactivity, albeit reduced, against BoNT/B LC. Such a finding is not unprecedented. The two inhibitors described by Tang et al. (47) were also reported to inhibit BoNT/B LC at concentrations >20 µM. Interestingly, all five compounds (at 240 µM) failed to inhibit BoNT serotype E light chain. This finding seems to suggest that they are more selective to serotype A.

It is also significant that efficacy of these candidate inhibitors was observed against BoNT/A holotoxin in cellular assays. Cells treated with all five compounds showed protection from the deleterious effects BoNT/A had on SNAP-25 at concentrations lower than the effective levels of previously reported small-molecule inhibitors (5, 9, 15). Of further importance is the observation that these five compounds exhibited little or no cell toxicity, a characteristic that is highly desirable in the development of a therapeutic drug. Unlike several BoNT/A small-molecule inhibitors that were reported cytotoxic at >5 µM (15) or >40 µM (9), four of the compounds (NSC 84096, CB 7969312, NSC 84094, and CB 7967495) were well-tolerated by the cells at concentrations up to 50 µM, and one (CB 7968218) exhibited signs of toxicity (aggregation and detachment of N2a cells from the plate surfaces) only at concentrations above 45 µM.

The findings in the tissue-based assay revealed that all five compounds were highly effective in the MPNHDA, significantly delaying the BoNT/A-induced paralytic half-time by at least threefold, while the peptide BoNT/A inhibitor Ac-CRATKML-NH$_2$ (SEQ ID NO: 1) was not protective. Among the five lead inhibitors, CB 7969312 was the most effective, at 0.5 µM. This striking observation represents CB 7969312 to be the most potent small-molecule BoNT/A inhibitor reported to date that exhibited activity in a tissue-based assay. While the in vivo mouse bioassay is preferred for evaluating the efficacy of candidate BoNT inhibitors, during the early phase of drug discovery and development, the ex vivo MPNHDA has a potential over the in vivo assay in that it requires only two mice per sample tested, and the results can be available within hours.

The effectiveness of these inhibitors in the in vitro and ex vivo assays was only demonstrated when the compound was premixed with BoNT/A toxin; pre-loading the inhibitor did not protect cells/tissues against BoNT intoxication. To date, no one is known to have been able to provide experimental evidence showing that inhibitors work in a pre-loading system. The small-molecule inhibitor that was reported to be active in primary neurons (9) was demonstrated to show a dose-dependent inhibition of SNAP-25 cleavage in a non-pre-loading system (cells were pretreated with inhibitor for 45 minutes followed by incubation with BoNT/A in the continuous presence of inhibitor). Additionally, the inhibitors reported by Eubanks et al. (15) and Boldt et al. (7) were characterized in cell culture assays that involved mixing BoNT/A toxin and varying concentrations of inhibitor.

The small-molecule inhibitors identified herein have three aromatic groups, one of which is an 8-quinolinol moiety. Quinolinol is known to chelate divalent cations (14) and also has antimicrobial properties (18, 19). Because of potential indiscriminate metal chelation, the 8-hydroxyquinoline motif has been tagged as a "not suitable" functional component of BoNT/A LC inhibitors (11). However, the particular class of quinolinol identified herein (with the other two ring systems and a secondary amine, see Tables 2 and 3) displayed specificity for BoNT serotype A and did not inhibit simply by chelating active-site zinc.

The structures of the quinolinol derivatives also contain additional basic moieties, including 2-amino or 3-amino pyridine (NSC 84094, CB 7967495, CB 7968218, and CB 7969312). The presence of these structural motifs suggests that these lead inhibitors may interact with the hydrophobic pocket located in the active site of the LC (see FIG. 4). Adler et al. (1) reported that the quinolinol moiety alone in the presence of zinc did not inhibit the proteolytic activity of BoNT serotypes A and B.

Figure 4:
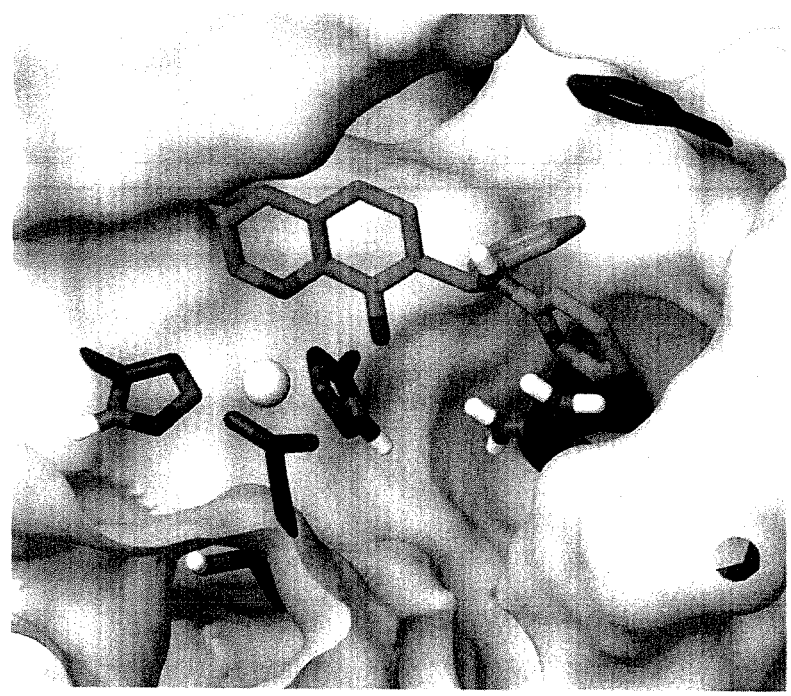
FIG. 4. Binding mode of NSC 84094 into BoNT/ALC substrate binding cleft showing the quinolinol group (light green) interacting with the Zn atom (light blue), while the pyridyl substituent can form hydrogen bond with Arg363. Atom colors: nitrogen (blue), oxygen (red), hydrogen (white), enzyme C atoms (dark green) and inhibitor C atoms (light green).

While the mechanism by which these newly identified small-molecules inhibit BoNT/A is still being elucidated, molecular docking provided key insights into the likely binding sites and mode of inhibition. As shown in FIG. 4, NSC 84094 is docked in the large hydrophobic pocket of the BoNT/A LC active site, and its hydroxyquinoline moiety coordinates with zinc, which could explain the importance of this group in inhibiting BoNT/A LC, and suggests that the quinolinols inhibit BoNT/A by blocking the active site zinc. Additionally, the pyridyl ring can form a hydrogen bond with Arg363, and may contribute to the specificity and potency of the inhibitor. It should be noted that the crystal structures of the complexes of known small-molecule and peptide inhibitors with BoNT/A LC have shown that chelation to zinc is involved in the binding and inhibition of the light chain in both cases (45, 46). A small molecule inhibitor reported to have some in vivo efficacy (15) is a zinc chelator (5). Chelation appears to be a necessary but not sole condition of known inhibitors. Further studies are warranted to fully determine the precise mechanism of action of these compounds.

In summary, the five small-molecule compounds represent highly potent, non-toxic BoNT/A inhibitors that were identified using an integrated screening strategy. These compounds effectively inhibited the protease activities of both BoNT/A LC (full-length and truncated), and also significantly neutralized BoNT/A holotoxin in N2a cells and hemidiaphragm assays. Such protection at the cellular and tissue levels is particularly important, since previously reported potent BoNT/A LC inhibitors such as Ac-CRATKML-NH$_2$ (SEQ ID NO: 1) were ineffective under these conditions. Moreover, the effective inhibition by these compounds of BoNT/A LC, but not BoNT/E LC, as well as their reduced efficiency of BoNT/B LC, suggest that these small-molecules preferentially interact with BoNT/A LC.

Pharmaceutical Preparations

Examples of a pharmaceutically acceptable carrier that may be used for preparation of the compositions of the present invention include various organic or inorganic carriers that are conventionally used as a pharmaceutical material. For example, excipients, lubricants, binders and disintegrators can be used for solid preparations; and solvents, solubilizing agents, suspending agents, isotonic agents, buffer agents, soothing agents, etc., can be used for liquid preparations. If necessary, conventional additives such as preservatives, antioxidants, coloring agents, sweetening agents, adsorbing agents and wetting agents can be also used in an appropriate amount. Those of skill in the art will be familiar with the carriers, diluents, adjuvants, etc. that are recommended for the subject to whom compositions of the invention are to be administered.

Administration to a Subject

Similarly, those of skill in the art will recognize that the preferred dosage to be administered to a subject will depend upon the species, gender, age, weight, and other health aspects of the subject. In addition, if the compositions of the invention are administered as part of a combination therapy for botulism or infection by a *C. botulinum*, the effects of the other therapeutic substances, alone and in combination, must be considered in determining the proper dosage and time of administration to the subject.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Initial test compounds were obtained from the Drug Synthesis and Chemistry Branch, Developmental Therapeutics Program, Division of Cancer Treatment and Diagnosis, National Cancer Institute (NCI; Bethesda, Md.), Sigma-Aldrich (St. Louis, Mo.) and Chembridge (CB) Corporation (San Diego, Calif.). Compounds that passed the preliminary HPLC screening were synthesized and purified by GLSynthesis, Inc. (Worcester, Mass.). The chemical structure and purity (>98%) of these analogs were verified and confirmed by LC-MS and NMR prior to use in subsequent assays. Molecular weights of the compounds were confirmed by mass spectrometry. All compounds tested were racemic mixtures.

The BoNT/A peptide inhibitor (Ac-CRATKML-NH$_2$) (SEQ ID NO: 1) was purchased from EMD Chemicals, Inc. (La Jolla, Calif.). Recombinant full-length BoNT/A and BoNT/B LCs were prepared according to procedures previously described by Gilsdorf et al. (20) and Jensen et al. (24), both of which are incorporated by reference, and were >97% pure based on SDS-PAGE gels. The recombinant light chain for the type E neurotoxin (rELC; residues 1-423, SEQ ID NO: 8) and truncated type A light chain (tALC, residues 1-425, SEQ ID NO: 6) were cloned, expressed, and purified. Briefly, rELC is encoded by the nucleotide sequence provided in SEQ ID NO: 7; tALC is encoded by the nucleotide sequence provided in SEQ ID NO: 5. rELC with a C-terminal 6×His-tag, and tALC were cloned and expressed in *E. coli* (pET24a+/BL21(DE3)). Purification of rELC was by affinity chromatography, followed by anion exchange chromatography. Purification of tALC involved a three-step ion exchange chromatography using Poros HS, Poros HQ, and Source 15S columns. The purity of rELC and tALC exceeded 90% and 97%, respectively, as judged by SDS/PAGE. Protein concentration was measured by BCA using BSA as a standard.

Botulinum neurotoxin serotype A (Hall strain) was obtained from Metabiologics (Madison, Wis.). The specific toxicity of the toxin was $2.4 \times 10^8$ mouse i.p. $LD_{50}$/mg of protein, as determined by a toxin titration procedure described previously (25). Synthetic peptides used as substrates for the HPLC assays were custom synthesized to >98% purity by Quality Controlled Biochemicals (Hopkinton, Mass.). The Alliance HPLC System (2695 XE Separation Module and 2996 Photodiode Array Detector) and the Empower/Millenium software were from Waters (Milford, Mass.). HPLC columns (Hi-Pore C18, 0.45×25 cm) were obtained from Bio-Rad Laboratories (Hercules, Calif.). Anti-SNAP-25 mouse monoclonal $IgG_1$ (SMI-81) was from CRP, Inc. (Berkeley, Calif.) and goat anti-mouse horseradish-peroxidase-conjugated was from KPL, Inc. (Gaithersburg, Md.). Cell culture media and reagents were from Lonza (Walkersville, Md.). ECL Advance Western Blotting Detection Kit was from GE Healthcare (Piscataway, N. J.). Tyrode's buffer was purchased from Sigma (St. Louis, Mo.).

Virtual Screening of BoNT/A Inhibitors

The three-dimensional structure of BoNT/A LC (PDB code: 1E1H) (39) obtained from the Protein Databank was used for virtual screening since it was the only suiTable 1 vailable crystal structure at the time the in silico screening was performed. One of the protomers was removed to vacate the active site. All water molecules were removed. Hydrogens and all-atom Kollman charges were added using the BIOPOLYMER module from SYBYL. The three-dimensional structures of small-molecules for docking were generated using Concord as implemented in SYBYL. DOCK 4.0 (16) was used for docking. Zinc parameters were optimized using the same training set as described by Hu et al. (23). In all cases, the scoring grids were defined to include the whole active site around the Zn. Ligand fitting with DOCK was employed using anchor-first docking with matching receptor sites, and using 25 peripheral seeds, 500 orientations, and uniform sampling. Anchors were first minimized, followed by layer 2 and the whole ligand. Ten thousand minimization steps were done for further refinement. All-atom representation and Gasteiger-Marsili empirical atomic partial charges were used for the ligands.

HPLC-Based BoNT/A and BoNT/B LC Protease Assays

Selected compounds from virtual screening were tested in HPLC-based BoNT/A LC and BoNT/B LC enzymatic assays as described previously by Gul et al. (21) and Schmidt and Bostian (37), both of which are incorporated herein by reference. The BoNT/A LC assay mixture contained 50 mM HEPES (pH 7.3), 0.8 mM substrate containing residues 187-203 of SNAP-25 (Ac-SNKTRIDEAN-QRATKML-NH$_2$) (SEQ ID NO: 2) (37), test compound dissolved in dimethylsulfoxide (DMSO) at 10× the final assay concentration, and 4.5-6.0 µg/mL (110-140 nM) BoNT/A LC. The LC catalyzes the hydrolysis of SEQ ID NO: 2 between residues Q11 and R12 corresponding to residues Q11 and R12 corresponding to residues 197 and 198 of SNAP-25.

The BoNT/B LC reaction mixture contained 50 mM HEPES buffer (pH 7.3), 0.4 mM substrate corresponding to residues 60-94 of human VAMP-2 (Ac-LSELD-DRADALQAGASQFETSAAKLKRKYWWKNLK-NH$_2$) (SEQ ID NO: 3)(44), 1 mM DTT, test compound in DMSO and 1.5-2 µg/mL (30-40 nM) BoNT/B LC. The LC catalyzes the hydrolysis of SEQ ID NO: 3 between residues Q17 and F18, corresponding to residue 76 and 77 of human VAMP-2. In control assays, the test compound was replaced by DMSO. The reaction was immediately mixed upon adding the light chain, and incubated at 37° C. for 5 min. Assays were stopped by acidification with 90 µl of 0.7% trifluoroacetic acid (TFA). The amount of uncleaved substrate and products were then measured after separation by reverse-phase HPLC. Solvent A was 0.1% TFA and solvent B was 70% acetonitrile/0.1% TFA. For assays with SEQ ID NO: 2, the flow rate was 1.0 mL/min. at 25° C., with a gradient profile of 10% B (2.5 min.), linear gradient to 36% B (21 min.), and 100% B (6 min.). For assays with SEQ ID NO: 3 the flow rate was 1.0 mL/min. at 25° C., with a gradient profile of 20% B (2.5 min.), linear gradient to 80% B (21 min.), and 100% B (6 min.).

HPLC-Based BoNT/A and/B Holotoxin Assay

The BoNT/A toxin assay was based on the method developed by Schmidt and Bostian (37) with some modification. Specifically, bovine serum albumin (BSA) was only used as a component of the buffer to dilute the toxin, hence its final concentration in the assay was reduced from 1 mg/ml to 167 µg/ml. Sukonpan et al. (50) reported that BSA binds to a number of organic compounds and could mask the identification of potential inhibitors. Briefly, the assay mixture contained 30 mM HEPES buffer (pH 7.3), 0.5 mM dithiothreitol, 0.25 mM $ZnCl_2$, 167 µg/ml of BSA, 0.8-0.9 mM substrate, 200 µM test compound in DMSO, and 335 nM of BoNT/A toxin. Immediately upon adding the holotoxin, each reaction mixture was mixed and incubated at 37° C. for 30 min. the reaction was stopped by acidification with trifluoroacetic acid (TFA). The amount of uncleaved substrate and products were then measured after separation by reverse-phase HPLC.

The BoNT/B toxin assay is similar to the BLC assay described above with the following modifications: a) the BLC was replaced by BoNT/B toxin diluted in 0 mM HEPES, pH 7.2+10 mM DTT+20 µM $ZnCl_2$; final B toxin concentration in the assay was 5.5. nM, and b) the reaction mixture was mixed and incubated at 37° C. for 30 minutes.

Determination of the $IC_{50}$

The 50% inhibitory concentration ($IC_{50}$) values against BoNT/A LC were calculated from nine concentrations of compound by a log-probit analysis program using the statistical software GraphPad Prism 4 (GraphPad Software, La Jolla, Calif.).

SNAP-25 Gel Cleavage Assay by Recombinant Light Chain E (rELC)

Thirteen µM recombinant SNAP-25 (List Biological Laboratories, Inc., Campbell, Calif.) was incubated with 6 µM recombinant BoNT/E LC (rELC) and 200 µM compound (dissolved in DMSO at 10× the final assay concentration), and incubated at 37° C. for 30 min. The positive control had rELC and DMSO. Inhibitors (240 µM) and rELC (6.0 µM) were added to recombinant SNAP-25 (S25; 12.9 µM) and incubated at 37° C. for 30 min. Reactions were stopped by adding SDS-PAGE buffer and heating for 5 min at 70° C. Samples were run on 12% Nu-PAGE Bis Tris gels (Invitrogen, Carlsbad, Calif.) and stained by Simply Blue (Invitrogen, Carlsbad, Calif.) (see FIG. 2A).

Carboxypeptidase A (CPA) Assay

The CPA plate assay was performed according to manufacturer's (Sigma, St. Louis, Mo.) recommendation. Briefly, the mixture contained sample reaction buffer, ultrapure water, varying concentrations of compounds dissolved in DMSO, and CPA. The positive control had CPA and DMSO, and the negative control contained CPA+CPA inhibitor from potato tuber. The plate was incubated for 5 minutes at 25° C. and the reaction was stopped by the addition of stop solution. The absorption at 350 nm was read and CPA activity was calculated. Percent inhibition was determined by comparing the CPA activity produced in the reactions with CPA alone and reactions containing CPA+test compound. Values are averages of two independent determinations, each in triplicate.

Cell Culture Assay

The cell culture assay was based on the procedures of Yowler et al. (49) and Boldt et al. (7), both of which are incorporated by reference herein. Briefly, cells of the murine cholinergic neuroblastoma cell line Neuro-2a (N2a) (ATCC # CCL-131) were incubated in Eagle's Minimum Essential Medium (EMEM) supplemented with 10% fetal bovine serum (FBS), 10 mM HEPES, 1% L-glutamine, 100 U/ml penicillin, and 100 µg/ml of streptomycin, in a 75-cm$^2$ cell culture flask at 37° C. in an atmosphere of 5% $CO_2$ and 95% air. Upon reaching 70-80% confluency, the medium was removed and the cells were washed with Dulbecco's phosphate-buffered saline (DPBS) without $Ca^{++}$ or $Mg^{++}$. Cells were pelleted, diluted to $1.5 \times 10^5$ cells/ml and plated in 6-well cell culture plates (2 ml/well). After incubation for 48 h at 37° C. in an atmosphere of 5% $CO_2$ and 95% air, the medium was removed and replaced with serum-free medium, and the cells were grown for an additional 24 h.

The inhibitor (0.6-0.9 µl of the initial stock of 16.7 mM in 100% DMSO) was mixed with 1.5 µl BoNT/A (1 mg/ml) in a total volume of 2.4 µl and incubated for 30 min at 37° C. The toxin+DMSO (control) or toxin-inhibitor mixture was added to 1 ml of EMEM without FBS to bring the final concentration of BoNT/A toxin to 10 nM. The concentration of BoNT/A was calibrated to produce ≥50% cleavage of the substrate SNAP-25 in a 24 h incubation at 37° C. In all samples, including controls, the final concentration of DMSO was ≤0.09%.

At the end of the incubation, the medium was removed, and the cells were lysed with CelLytic™ M (Sigma, St. Louis, Mo.). Samples were run on 12% NuPAGE Bis-Tris gels (Invitrogen) and subjected to western blot analysis (see FIGS. 2B and 2C) using anti SNAP-25 monoclonal antibody (CRP, Inc.), followed by goat anti-mouse horseradish-peroxidase-conjugated secondary antibody (KPL, Inc.). Samples were visualized using ECL Advance Western Blotting Detection Kit (GE Healthcare). Signals were quantitated using the UN-SCAN-IT Gel™ software (Silk Scientific, Orem, Utah). Data presented are representative of results from three independent assays.

Mouse Phrenic Nerve Hemidiaphragm Assay (MPNHDA)

The MPNHDA was conducted based on the procedures of Sheridan et al. (42), incorporated herein by reference. Female CD-1 mice (20-25 g) were euthanized with $CO_2$ and their diaphragms with attached phrenic nerves were removed. The diaphragms were then divided into two hemidiaphragms with each section complete with a phrenic nerve and myoneural junction. Each hemidiaphragm was attached to an isometric force transducer (Fohr Medical Instruments, Seeheim, Germany), and its phrenic nerve was secured to a stimulating electrode. The nerve-muscle preparations were immersed in separate 10-ml tissue baths containing Tyrode's buffer (1.8 mM $CaCl_2$, 1 mM $MgCl_2$, 2.7 mM KCl, 137 mM NaCl, 0.4 mM $NaH_2PO_4$, 12 mM $NaHCO_3$, and 6 mM glucose), pH 7.2-7.4 (Sigma, St. Louis, Mo.). A mixture of 95% air/5% $CO_2$ gas was passed through the Tyrode's buffer. The tissue baths were kept at 37° C.

Each phrenic nerve was stimulated with single supramaximal pulses (SD9 Stimulators Grass Instruments, Warwick, R.I.) through a Powerlab/4 sp and Bridge Amp relay (ADInstruments, Inc., Colorado Springs, Colo.) of 0.3 msec duration at 0.03 Hz. The twitch tensions were digitally recorded by Chart software (ADInstruments, Inc., Colorado Springs, Colo.) Maximal twitch tensions were adjusted to 0.75-1.0 g, and the samples were run for 20-30 min to reach a sTable 2aseline. The inhibitor (dissolved in DMSO at 2× the final assay concentration) was mixed with 60 µM BoNT/A (Metabiologics, Madison, Wis.) in 5 ml of Tyrode's buffer and incubated for 15-20 min at 37° C. After baseline stabilization, the toxin-inhibitor mixture was added to a 10-ml bath with an additional 5 ml of Tyrode's buffer, bringing the final concentration of BoNT/A toxin to 30 pM. The concentration of BoNT/A neurotoxin was previously calibrated to induce a 50% loss of twitch tension in approximately 60 min. In all samples, including the controls, the final concentration of DMSO was 0.3%.

For each experiment, four tissue baths were used. One bath was the BoNT/A toxin-only control. A second bath was an assay control without toxin or inhibitor. The third and fourth baths contained toxin plus two different concentrations of inhibitor. Adding the toxin or the toxin/inhibitor mixture to the bath initiated the beginning of data collection, which continued for 5 h or until muscle twitch tension ceased.

For all preparations, neurotoxin-induced paralysis was measured as a 50% loss of twitch tension evoked by nerve stimulation. Estimates of statistical significance were based on unpaired, two-tailed t-test, with a P value of <0.05 considered significant, as previously reported (13, 42, 43). Statistical analysis was performed using SigmaPlot 10 (Systat Software, San Jose, Calif.).

Procedures used to obtain mouse tissues were conducted in compliance with the Animal Welfare Act and other U.S. federal statutes and regulations relating to animals and experiments involving animals, and adhered to principles stated in the Guide for the Care and Use of Laboratory Animals, National Research Council, 1996. The facility where this research was conducted is fully accredited by the Association for Assessment and Accreditation of Laboratory Animal Care International.

Procedure for the Synthesis of 84094 Analogs

The general synthesis procedure is described in Fernando et al. (16a) and Phillips (32a), both of which are incorporated herein by reference. Briefly, these synthetic targets are accessed via the Betti reaction, a one step single pot reaction that is a modification of classic Mannich chemistry. The desired aromatic amine (1.0 mmol) is dissolved in 3 mL of ethanol in a small flask. To this, the desired aldehyde (1.0 mmol) is added dropwise. The solution was allowed to stand for 15 to 20 minutes to promote the formation of the Mannich base. The desired quinolinol (1.0 mmol) is then dissolved in a minimal amount of ethanol with gentle heating, and the resulting solution is added to the reaction flask. The reaction mixture is then allowed to stand until solid precipitate forms, or until thin layer chromatography indicates that no further product is being formed. In the case of limited solubility of the reagents or nucleophilicity of the amine component, a microwave reactor is used. Depending upon the reactants used the timeframe for the precipitation of solid product ranges from a few hours to several months. Purification of the solid precipitate or the crude reaction mixture via reverse-phase vacuum liquid chromatography using gradient elution with MeCN—$H_2O$ mixtures yields the pure desired product in moderate to high yield.

Example 1: Identification of Small-Molecule Inhibitors of Botulinum Neurotoxins

The flow chart shown in FIG. 1 outlines the overall strategy for the identification of small-molecule inhibitors of BoNT/A. Focus was placed on serotype A since it is the most prevalent and well-studied among the various serotypes in human intoxication. In silico screening was used to identify BoNT/A inhibitors. Selected compounds were tested for inhibition of the protease activity of BoNT/A LC. Compounds that passed the HPLC screens were advanced to in vitro and ex vivo assays.

Virtual Screening of the NCI Database

The NCI database was chosen for virtual screening on the basis of the following considerations. First, it constitutes the largest freely available, public domain chemical structure database with >250,000 compounds (48). Second, it contains a high number of unique and structurally diverse compounds. Thus, the NCI database provides an opportunity to discover lead compounds (48).

The compounds from the NCI database were docked into the active site in one of the protomers of BoNT/A LC (PDB code: 1E1H) (39) after removing the peptide occupying the active site in the protomer. The top scoring 500 compounds were evaluated in more detail; the list was narrowed to 100 structurally-diverse compounds that interacted well with the active site Zn and demonstrated a good fit in the BoNT/A LC binding site.

HPLC-BoNT/A LC Protease Assay

Out of 100 tested, eight compounds were selected that inhibited BoNT/A, as well as, rALC by more than 60% and 30% at 200 µM and 20 µM, respectively (Table 1). These compounds had diverse chemical structures with molecular weights ranging from 285 to 622. To determine the actual effectiveness of the compounds predicted by the virtual screening, an HPLC-based enzymatic assay was performed in the presence and absence of inhibitor at 20 µM and 200 µM using full-length recombinant BoNT/A LC (rALC). The substrate peptide for BoNT/A LC protease activity consisted of residues 187-203 of SNAP-25, SEQ ID NO: 2, and BoNT/A LC catalyzes the hydrolysis between residues Q197 and R198 (37). In this study, focus was placed on the quinolinol lead NSC 1010. Selection of this compound was based on: (1) NSC 1010 was very potent against rALC; (2) NSC 1010 failed to inhibit BoNT serotype B light chain (not shown), suggesting its selectivity for serotype A; (3) there are quinolinols in clinical trials for Alzheimer's disease and cancer (22, 33, 34); and (4) quinolinol-based drugs such as linolasept and vioform (generic name: clioquinol) are available in the market.

TABLE 1

Structures of selected hits and percent inhibition against recombinant full-length BoNT/A light chain (rALC)$^a$.

NSC 377386
MW = 404
(75, N/A)

TABLE 1-continued

Structures of selected hits and percent inhibition against recombinant full-length BoNT/A light chain (rALC)$^a$.

NSC 1010
MW = 371
(87, 52)

NSC 201872
MW = 536
(82, 49)

NSC 13585
MW = 302
(80, 44)

NSC 48442
MW = 395
(75, 37)

TABLE 1-continued

Structures of selected hits and percent inhibition against recombinant full-length BoNT/A light chain (rALC)[a].

NSC 96399
MW = 285
(65, 29)

NSC 217026
MW = 390
(75, 52)

NSC 658253
MW = 622
(85, 51)

[a]Structures were obtained from the NCI Developmental Therapeutics Program website (See world wide web page at dtp.nci.nih.gov/index.html/). Compounds were tested in an HPLC-based assay using recombinant full-length BoNT/A LC (140 nM) in the presence of 0.8 mM 17-mer SNAP-25 peptide substrate. Percentages of inhibition at 200 and 20 μM, respectively, are indicated in parentheses and were determined by the amounts of peptide substrate cleaved in the presence or absence of inhibitors under the same conditions.

Screening and Testing Analog Compounds

To verify chemical identity, NSC 1010 was synthesized, and its structure and purity confirmed using standard techniques in the art. Further evaluation of this compound revealed that it was toxic to neuroblastoma N2a cells in cellular assays at ≥10 μM. Similarity searches were performed of Sigma, Chembridge and NCI databases to look for non-toxic analogs. Fifty-five analogs were identified and synthesized; structures of the compounds that were highly potent against the protease activity of BoNT/A (>75% inhibition) are shown in Table 2. Testing of these analogs in HPLC-based assays demonstrated five analogs (NSC 84094, NSC 84096, CB 7967495, CB 7969312, and CB 7968218) to be more potent than the original hit NSC 1010 and, of equal importance, non-toxic to cells (see Table 3 below). These five analogs constitute the final compounds that were subsequently characterized in cell- and tissue-based assays (see Examples 2 and 3). These compounds are racemates. Whether one or both of the enantiomers contributed to the inhibition is unknown since the docking poses for the two enantiomers of NSC 84096 in the active site of BoNT/A LC were different but gave comparable scores (not shown).

TABLE 2

Two dimensional structures of compounds displaying >75% inhibition (at 200 μM concentration) against BoNT/A light chain. Identification numbers correspond to those assigned in the NCI and Chembridge databases.

NSC 84086

NSC 84094

CB 7967495

NSC 1010

TABLE 2-continued

Two dimensional structures of compounds
displaying >75% inhibition (at 200 μM
concentration) against BoNT/A light chain.
Identification numbers correspond to
those assigned in the NCI and Chembridge databases.

NSC 84090

NSC 84096

NSC 84087

NSC 84093

NSC 84087

CB 7969312

CB 7967601

CB 7967682

CB 7968687

TABLE 2-continued

Two dimensional structures of compounds displaying >75% inhibition (at 200 μM concentration) against BoNT/A light chain. Identification numbers correspond to those assigned in the NCI and Chembridge databases.

CB 7969312

CB 7969927

CB 7970161

CB 6372490

CB 7628245

CB 7633178

CB 6633504

CB 6637043

TABLE 2-continued

Two dimensional structures of compounds displaying >75% inhibition (at 200 µM concentration) against BoNT/A light chain. Identification numbers correspond to those assigned in the NCI and Chembridge databases.

CB 6381661

CB 7925368

CB 6378057

CB 6380823

CB 6636098

NSC 84093

CB 7968218

To compare the relative inhibitory potencies of the five analogs, HPLC-based assays were performed using two recombinant forms of BoNT/A light chain: full-length (rALC) and truncated (1-425; tALC). Under assay conditions, rALC was at least 4× more active than tALC. The five analogs were very effective against both forms of BoNT/A LC, demonstrating IC$_{50}$ values ranging from 1.6-4.7 µM and 1.5-5.0 µM for rALC and tALC, respectively (Table 3).

TABLE 3

Structural formula and IC$_{50}$ values of selected analogs against recombinant full-length BoNT/A light chain (rALC) and truncated (1-425) A light chain (tALC)$^a$

NSC 84096
MW = 377
(3.2; 3.9)

NSC 84094
MW = 327
(1.6; 1.5)

CB 7967495
MW = 395
(4.7; 5.0)

CB 7968218
MW = 345
(3.9; 2.4)

CB 7969312
MW = 406
(2.1; 1.6)

$^a$Structures were obtained from the NCI Developmental Therapeutics Program website (see the world wide web page for dtp.nci.nih.gov/index.html/), and those of CB compounds were from Chembridge screening compounds and building blocks (see the world wide web page for hit2lead.com/). All compounds tested were racemates. The structure and purity of these analogs were confirmed by LC-MS and NMR.
The IC$_{50}$ values for rALC and tALC are indicated in parenthesis, respectively, and were determined from nine concentrations of each inhibitor using GraphPad Prism 4 (GraphPad Software, La Jolla, CA). rALC (140 nM final concentration) or tALC (620 nM) was incubated with 0.8 mM 17-mer SNAP-25 peptide substrate and varying concentrations of inhibitor (dissolved in DMSO at 10X final concentration) at 37° C. for 5 min in 50 mM HEPES, pH 7.3.
Reactions were stopped by adding 0.7% TFA and analyzed by reverse-phase HPLC.

Having established that these five analogs were very potent against BoNT/A LC, their effects were tested on two related BoNT endopeptidases: recombinant full-length BoNT/B light chain (rBLC) and BoNT/E light chain (rELC). The five compounds showed cross-reactivity against rBLC, with both NSC 84096 and NSC 84094 exhibiting the least inhibition at 6.9% and 8.8%, respectively (Table 4). However, none of the compounds (at 240 mM) inhibited rELC in gel cleavage assays (FIG. 2A). Although additional BoNT light chain serotypes would need to be tested before concluding that these five compounds are more selective for BoNT/A, this possibility deserves consideration.

TABLE 4

Percent inhibition of selected small-molecules against recombinant BoNT/A light chain (rALC) and BoNT/B light chain (rBLC) $^a$

| | % Inhibition Against | | | |
|---|---|---|---|---|
| Compound | rALC | rBLC | BoNT/A | BoNT/B |
| NSC 84096 | 91.9 ± 1.7 | 6.9 ± 2.0 | 77.8 ± 2.0 | 55.0 ± 0.1 |
| NSC 84094 | 97.4 ± 2.2 | 8.8 ± 0.8 | 85.1 ± 0.4 | 77.1 ± 0.0 |
| CB 7967495 | 92.7 ± 1.5 | 30.2 ± 2.4 | 90.6 ± 2.2 | 86.8 ± 0.0 |
| CB 7968218 | 92.8 ± 0.8 | 16.8 ± 2.2 | 95.6 ± 2.1 | 90.2 ± 0.0 |
| CB 7969312 | 96.2 ± 1.2 | 31.2 ± 3.0 | 71.0 ± 0.7 | 85.0 ± 0.0 |

$^a$ HPLC-based protease assays were conducted at 37° C. using various inhibitors at 20 μM final concentration. rALC assays contained 50 mM HEPES (pH 7.3), 0.8 mM SNAP-25 peptide substrate, test compound in DMSO, and rALC (110-140 nM). The assay for rBLC contained 50 mM HEPES (pH 7.3), 1 mM DTT, 0.4 mM 35-mer VAMP peptide substrate, test compound in DMSO, and rBLC (30-40 nM). Inhibitors were diluted into the reaction mixture containing the substrate, followed by the addition of LC (i.e., inhibitor and LC were not pre-incubated). Reactions were stopped by acidification by TFA, and analyzed by reverse-phase HPLC. Data represent mean ± SD from 2 independent assays.

Further experimental studies revealed that all five compounds (at concentrations up 20 μM) showed no inhibitory effect on the zinc protease carboxypeptidase (CPA), while the control inhibitor from potato tuber exhibited 100% inhibition at concentrations equal to or greater than 0.187 μM (not shown). This finding precludes the possibility that the inhibition of BoNT/A endopeptidase by these analogs was due to nonspecific chelation.

Further synthesis and testing of novel analogs of NSC 1010 provided new chemical entities with comparable or improved potency (Table 5).

TABLE 5

Previously unreported analogs with potent activity against BoNT/A

| Compound | Chemical Structure | % Inhibition against BoNT/A (5 μM) | IC$_{50}$ (μM) |
| --- | --- | --- | --- |
| 5116-047A | 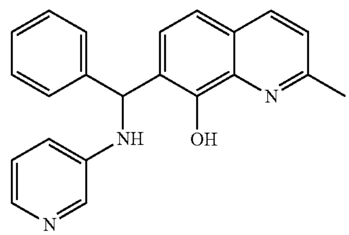 [SMILES: Cc1ccc2ccc(C(Nc3cccnc3)c3ccccc3)c(O)c2n1] | 83.0 | 1.4 |
| 5116-048A | 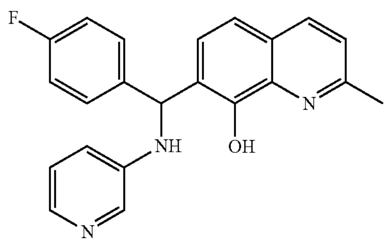 [SMILES: Cc1ccc2ccc(C(Nc3cccnc3)c3ccc(F)cc3)c(O)c2n1] | 87.0 | 0.8 |
| 5116-050A | 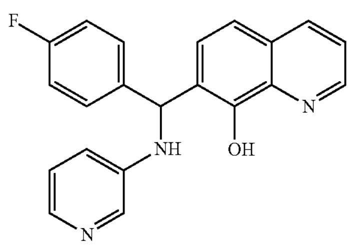 [SMILES: Oc1c(C(Nc2cccnc2)c2ccc(F)cc2)ccc2cccnc12] | 86.7 | 1.2 |
| 5116-051A | 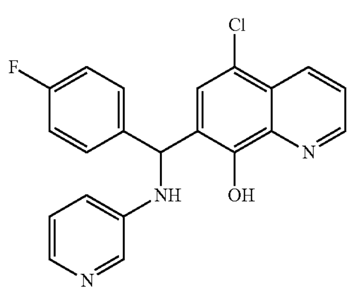 [SMILES: Oc1c(C(Nc2cccnc2)c2ccc(F)cc2)cc(Cl)c2cccnc12] | 91.0 | <1.0 |
| 5116-052A | 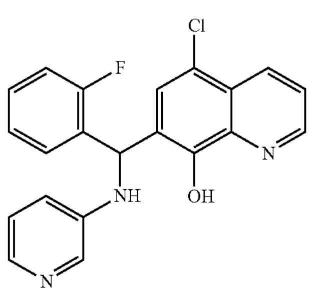 [SMILES: Oc1c(C(Nc2cccnc2)c2ccccc2F)cc(Cl)c2cccnc12] | 97.5 | <1.0 |

TABLE 5-continued

Previously unreported analogs with potent activity against BoNT/A

| Compound | Chemical Structure | % Inhibition against BoNT/A (5 μM) | IC$_{50}$ (μM) |
|---|---|---|---|
| 4874-051A | (structure: quinoline with NH$_2$, OH, and CH-phenyl with NH-pyridine substituents) | 94.0 | 2.2 |

Example 2: Inhibition in Cell-Based Assay

To this point, it has been demonstrated that five compounds inhibit the enzymatic activity of BoNT/A in vitro. To examine the likelihood that these compounds might be useful antibotulinum therapeutics, studies were performed in other systems. One of these used murine neuroblastoma N2a cells to evaluate the ability of these compounds to protect BoNT/A-mediated cleavage of intracellular SNAP-25. BoNT/A binds to N2a cells and the translocated LC cleaves SNAP-25 in these cells. The extent of cleavage of SNAP-25 in N2a cells by BoNT/A was determined by western blot analysis using monoclonal antibodies against SNAP-25. As shown in FIG. 2B, all five lead analogs at 15 μM, exhibited complete protection of BoNT/A-mediated SNAP-25. At 10 μM three of these compounds (CB 7967495, NSC 84094, CB 7969312) showed near-to-complete inhibition of SNAP-25 cleavage while the other two (NSC 84096 and CB 7968218) afforded 66% and 68% protection, respectively (FIG. 2C).

Example 3: Activity in Mouse Phrenic Nerve Hemidiaphragm Assay

Encouraged by these findings, the efficacy of these analogs was examined at the tissue level using mouse phrenic nerve hemidiaphragm preparations whose intact neuromuscular junction permits the monitoring of the effectiveness of an inhibitor by recording muscle twitch tension. In the ex-vivo mouse phrenic nerve hemidiaphragm assay (MPN-HDA), the time to onset of neuromuscular block is a concentration-sensitive event, with blockade occurring earlier with higher toxin concentrations (13, 40, 41). Changes in the onset of muscle paralysis with a fixed concentration of toxin are used to indicate the activity of candidate BoNT therapeutics.

Figure 3:
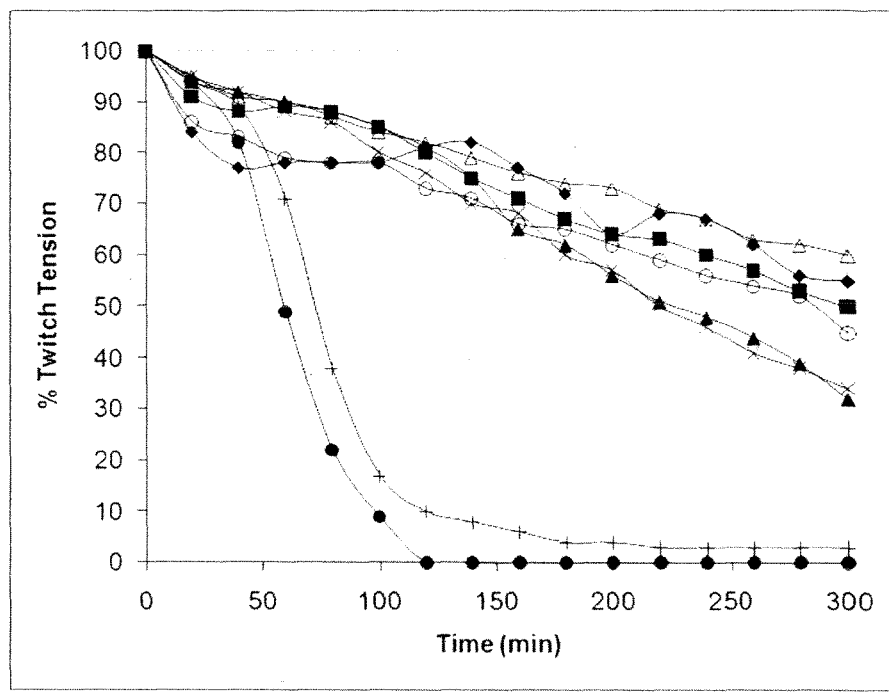
FIG. 3. Effects of BoNT/A small-molecule inhibitors in mouse phrenic nerve hemidiaphragm assay (MPNHDA). In all assays, BoNT/A (+) and No Toxin (Δ) controls were run to demonstrate the difference in twitch tension between BoNT-intoxicated and normal tissues (n=18 for both groups). The twitch tension time courses are the averages of triplicate assays. The time courses include only the effective concentration of inhibitor required for maximum protection, except for CRATKML which was not effective at the tested concentration: (■) CB 7969312 (500 nM), (▲) CB 7967495 (5 µM), (○) NSC 84094 (10 µM), (♦) CB 7968218 (10 µM), (x) NSC 84096 (20 µM), and (●) CRATKML (20 µM).

Results from MPNHDA experiments demonstrated that applying effective concentrations of compounds significantly delayed (P<0.01) the onset of toxin-induced paralysis (Table 6). While neuromuscular preparations exposed to BoNT/A alone (control) produced an average paralytic time of 65.7±7.80 min, those that were exposed to inhibitors at effective concentrations ranged from 216.3-281.0 min. The effective concentrations that caused a delay in time to 50% loss of twitch tension for the five inhibitors ranged from 0.5 μM-20 μM. Moreover, the muscle twitch-tension time courses of the five inhibitors at their effective concentrations during the entire assay period (300 min) were comparable to the No Toxin-control group (FIG. 3). By comparison, the peptide BoNT/A inhibitor Ac-CRATKML-NH$_2$ (SEQ ID NO: 1) (K$_i$=1.9 μM) (38) did not cause a delay in paralytic time at 20 μM, and showed muscle twitch-tension time courses that were similar to that of BoNT/A alone (control) (FIG. 3). This is the first report of BoNT/A small-molecule inhibitors that showed activity in an ex vivo assay.

TABLE 6

Effect of small-molecule inhibitors in protecting BoNT/A-induced neuromuscular block in mouse phrenic nerve hemidiaphragm assays.

| Inhibitor | Concentration (μM) | Average Time to 50% Loss of Twitch Tension (min)[a] |
|---|---|---|
| Without BoNT/A | — | >300.00 |
| With BoNT/A | — | 65.70 ± 7.80 |
| BoNT/A + NSC 84096 | 20.0 | 216.3 ± 20.2[b] |
|  | 0.10 | 59.7 ± 4.9[d] |
| BoNT/A + NSC# 84094 | 10.0 | 266.3 ± 19.6[b] |
|  | 0.25 | 72.0 ± 5.5[c] |
| BoNT/A + CB 7967495 | 5.00 | 216.3 ± 25.2[b] |
|  | 1.00 | 58.7 ± 7.5[c] |
| BoNT/A + CB 7968218 | 10.0 | 281.0 ± 19.0[b] |
|  | 0.10 | 66.3 ± 10.6[c] |
| BoNT/A + CB 7969312 | 0.50 | 271.0 ± 29.0[b] |
|  | 0.10 | 91.7 ± 19.6[c] |
| BoNT/A + SEQ ID NO: 1 | 20.0 | 52.70 ± 9.30[c] |
|  | 5.00 | 65.0 ± 11.5[c] |

[a]Specified concentrations of small-molecule inhibitors and BoNT/A were added to hemidiaphragm preparations, and isometric contractions of the electrically-stimulated muscles were recorded and analyzed. The time required to 50% of loss of twitch tension (paralytic half-time) was determined. Controls (with and without BoNT/A) used the same amount of DMSO (0.3% final concentration) as those with inhibitors. Data are means ± SE (n = 3 for small-molecules and Ac-CRATKML-NH$_2$ (SEQ ID NO: 1); n = 18 for With BoNT/A and without BoNT/A control groups).
[b]P < 0.01, highly significant;
[c]P > 0.05, not significant from those recorded with BoNT/A control. Statistical analysis was performed using SigmaPlot 10 (Systat Software, San Jose, CA).
[d]P > 0.05, not significant from those recorded with BoNT/A alone. Statistical analhysis was performed using SigmaPlot 10.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

REFERENCES

The following references, to the extent that they provide exemplary procedural or other details supplementary to those set forth herein, are specifically incorporated herein by reference.

1. Adler, M., R. E. Dinterman, and R. W. Wannemacher. 1997. Protection by the heavy metal chelator N,N,N',N'-tetrakis (2-pyridylmethyl)ethylenediamine (TPEN) against the lethal action of botulinum neurotoxin A and B. Toxicon 35: 1089-1100.
2. Associated Press. Jul. 24, 2007, posting date. Castleberry expands food recall over link to botulism outbreak. Available on the world wide web at foxnews.com/story/0,2933, 290507,00.html.
3. Black, J. D., and J. O. Dolly. 1986. Interaction of 125I-labeled botulinum neurotoxins with nerve terminals. I. Ultrastructural autoradiographic localization and quantitation of distinct membrane acceptors for types A and B on motor nerves. J. Cell Biol. 103(2): 521-534.
4. Black, J. D., and J. O. Dolly. 1986. Interaction of 125I-labeled botulinum neurotoxins with nerve terminals. II. Autoradiographic evidence for its uptake into motor nerves by acceptor-mediated endocytosis. J. Cell Biol. 103(2): 535-544.
5. Boldt, G. E., J. P. Kennedy, and K. D. Janda. 2006. Identification of a potent botulinum neurotoxin A protease inhibitor using in situ lead identification chemistry. Org. Lett. 8: 1729.
6. Boldt, G. E., J. P. Kennedy, M. S. Hixon, L. A. McAllister, J. T. Barbieri, S. Tzipori, and K. D. Janda. 2006. Synthesis, characterization and development of a high-throughput methodology for the discovery of botulinum neurotoxin a inhibitors. J. Comb. Chem. 8(4): 513-521.
7. Boldt, G. E., L. M. Eubanks, and K. D. Janda. 2006. Identification of a botulinum neurotoxin A protease inhibitor displaying efficacy in a cellular model. Chem. Commun. (Camb.) 29: 3063-3065.
8. Breidenbach, M. A., and A. T. Brunger. 2004. Substrate recognition strategy for botulinum neurotoxin serotype A. Nature 432(7019): 925-929.
9. Burnett, J. C., G. Ruthel, C. M. Stegmann, R. G. Panchal, T. L. Nguyen, A. R. Hermone, R. G. Stafford, D. G. Lane, T. A. Kenny, C. F. McGrath, P. Wipf, A. M. Stahl, J. J. Schmidt, R. Gussio, A. T. Brunger, and S. Bavari. 2007. Inhibition of metalloprotease botulinum serotype A from a pseudo-peptide binding mode to a small-molecule that is active in primary neurons. J. Biol. Chem. 282: 5004-5014.
10. Burnett, J. C., J. J. Schmidt, C. F. McGrath, T. L. Nguyen, A. R. Hermone, J. L. Vennerstrom, K. Kodukula, D. W. Zaharevitz, R. Gussio, and S. Bavari. 2005. Conformational sampling of the botulinum neurotoxin serotype A light chain: implications for inhibitor binding. Bioorg. Med. Chem. 13: 333-341.
11. Burnett, J. C., J. J. Schmidt, R. G. Stafford, R. G. Panchal, T. L. Nguyen, J. L. Vennerstrom, C. F. McGrath, D. J. Lane, E. A. Sausville, D. W. Zaharevitz, R. Gussio, and S. Bavari. 2003. Novel small-molecule inhibitors of botulinum neurotoxin A metalloprotease activity. Biochem. Biophys. Res. Commun. 310: 84-93.
12. Capková, K., Y. Yoneda, T. J. Dickerson, and K. D. Janda. 2007. Synthesis and structure-activity relationships of second-generation hydroxamate botulinum neurotoxin A protease inhibitors. Bioorg. Med. Chem. Lett. 17(23): 6463-6466.
13. Deshpande, S. S., R. E. Sheridan, and M. Adler. 1995. A study of Zn-dependent metalloendopeptidase inhibitors as pharmacological antagonists in botulinum neurotoxin poisoning. Toxicon 33: 551-557.
14. Deshpande, S. S., R. E. Sheridan, and M. Adler. 1997. Efficacy of certain quinolines as pharmacological antagonists in botulinum neurotoxin poisoning. Toxicon 35: 433-445.
15. Eubanks, L. M., M. S. Hickson, W. Jin, S. Hong, C. M. Clancy, W. H. Tepp, M. R. Baldwin, C. J. Malizio, M. C. Goodnough, J. T. Barbieri, E. A. Johnson., D. L, Boger. T. J. Dickerson, and K. D. Janda. 2007. An in vitro and in vivo disconnect uncovered through high-throughput identification of botulinum neurotoxin A antagonists. Proc. Natl. Acad. Sci. USA 104: 2602-2607.
16. Ewing, T. J., S. Makino, A. G. Skillman, and I. D. Kuntz. 2001. DOCK 4.0: search strategies for automated molecular docking of flexible molecule databases. J. Comput. Aided Mol. Des. 15: 411-428.
16a. Fernando, Q., R. Keown, and J. P. Phillips. 1953. The reaction of aldehydes and aromatic amines with 8-quinolinol. J. Am. Chem. Soc. 75: 4306-4307.
17. Foran, P. G., B. Davletov, and F. A. Meunier. 2003. Getting muscles moving again after botulinum toxin: novel therapeutic challenges. Trends Mol. Med. 9: 291-299.
18. Gershon, H., and R. Pamegiani. 1962. Antimicrobial activity of 8-quinolinol, its salts with salicylic acid and 3-hydroxy-2-naphthoic acid, and the respective copper (II) chelates in liquid culture. Appl. Microbiol. 10: 62-65.
19. Gershon, H., and R. Pamegiani. 1962. Antimicrobial activity of 8-quinolinols, salicylic acids, hydroxynaphthoic acids, and salts of selected quinolinols with selected hydroxy-acids. Appl. Microbiol. 10: 556-560.
20. Gilsdorf, J., N. Gul, and L. A. Smith. 2006. Expression, purification, and characterization of Clostridium botulinum type B light chain. Protein Expr. Purif. 46(2): 256-267.
21. Gul, N., S. A. Ahmed, and L. A. Smith. 2004. Inhibition of the protease activity of the LC of type A botulinum neurotoxin by aqueous extract from stinging nettle (Urtica dioica) leaf. Basic Clin. Pharmacol. Toxicol. 95: 215-219.
22. Helmuth, L. 2000. Neuroscience: an antibiotic to treat Alzheimer's? Science 290: 1273-1274.
23. Hu, X., S. Balaz, and W. H. Shelver. 2004. A practical approach to docking of zinc metalloproteinase inhibitors. J. Mol. Graph. Model. 22: 293-307.
24. Jensen, M. J., T. J. Smith, S. A. Ahmed, and L. A. Smith. 2003. Expression, purification, and efficacy of the type A botulinum neurotoxin catalytic domain fused to two translocation domain variants. Toxicon 4: 691-701.
25. Kalb, S. R., T. J. Smith, H. Moura, K. Hill, J. Lou, I. N. Geren, C. Garcia-Rodriguez, J. D. Marks, L. A. Smith, J. L Pirkle, and J. R. Barr. 2008 The use of Endopep-MS to detect multiple subtypes of botulinum neurotoxins A, B, E, and F. Int J Mass Spectrom 278: 101-108.
26. Kongsaengdao, S., K. Samintarapanya, S. Rusmeechan, A. Wongsa, C. Pothirat, C. Permpikul, S. Pongpakdee, W. Puavilai, P. Kateruttanakul, U. Phengtham, K. Panjapornpon, J. Janma, K. Piyavechviratana, P. Sithinamsuwan, A. Deesomchok, S. Tongyoo, W. Vilaichone, K. Boonyapisit, S. Mayotarn, B. Piya-Isragul, A. Rattanaphon, P. Intalapaporn, P. Dusitanond, P. Harnsomburana, W. Laowittawas, P. Chairangsaris, J. Suwantamee, W. Wongmek, R. Ratanarat, A. Poompichate, H. Panyadilok, N. Sutcharitchan, A. Chuesuwan, P. Oranrigsupau, C. Sutthapas, S. Tanprawate, J. Orsuwansiri, N. Phattana; Thai Botulism Study Group. 2006. An outbreak of botulism in Thailand: clinical manifestations and management of severe respiratory failure. Clin. Infect. Dis. 43: 1247-1256.
27. Lacy, D. B., W. Tepp, A. C. Cohen, B. R. DasGupta, and R. C. Stevens. 1998. Crystal structure of botulinum neurotoxin type A and implications for toxicity. Nat. Struct. Biol. 5: 898-902.
28. McClatchy Newspapers. Jul. 24, 2007, posting date. Botulism cases spur huge food recall. Available on the world wide web at omaha.com/index.php?u_page=1100&u_sid=10086080#list.
29. Moe, S. T., A. B. Thompson, G. M. Smith, R. A. Fredenburg, R. L. Stein, and A. R. Jacobson. 2009. Botulinum neurotoxin serotype A inhibitors: small-molecule mercaptoacetamide analogs. Bioorg Med. Chem. 17(8): 3072-3079.
30. Montal, M. S., R. Blewitt, J. M. Tomich, and M. Montal. 1992. Identification of an ion channel-forming motif in the primary structure of tetanus and botulinum neurotoxins. FEBS Lett. 313(1): 12-18.
31. Montecucco, C., and G. Schiavo. 1995. Structure and function of tetanus and botulinum neurotoxins. Quart. Rev. Biophys. 28: 423-472.
32. Park, J. G., P. C. Sill, E. F. Makiyi, A. T. Garcia-Sosa, C. B. Millard, J. J. Schmidt, and Y. P. Pang. 2006. Serotype-selective, small-molecule inhibitors of the zinc endopeptidase of botulinum neurotoxin serotype A. Bioorg. Med. Chem. 14: 395-408.
32a. Phillips, J P. 1956. The reactions of 8-quinolinol. Chem. Rev. 56: 271-297.
33. PRNewswire. Apr. 17, 2007, posting date. Alzheimer's drug shows promise in fighting cancer. Available on the world wide web at drugs.com/clinical_trials/alzheimer-s-shows-promise-fighting-cancer-628.html?printable=1.
34. Ritchie, C. W., A. I. Bush, A. Mackinnon, S. Macfarlane, M. Mastwyk, L. MacGregor, L. Kiers, R. Chemy, Q. Li, A. Tammer, D. Carrington, C. Mavros, I. Volitakis, M. Xilinas, D. Ames, S. Davis, K. Beyreuther, R. E. Tanzi, C. L. Masters. 2003. Metal-protein attenuation with iodochlorhydroxyquin (Clioquinol) targeting Aβ amyloid deposition and toxicity in Alzheimer Disease, a pilot phase 2 clinical trial. Arch. Neurol. 60: 1685-1691.
35. Schiavo, G., and M. Montecucco. 1997. Clostridial neurotoxins, p. 169-186. In K. Aktories (ed.), Bacterial Toxins: Tools in Cell Biology and Pharmacology, Chapman and Hall, Weinheim, Germany.
36. Schiavo, G., O. Rossetto, and C. Montecucco. 1994. Clostridial neurotoxins as tools to investigate the molecular events of neurotransmitter release. Sem. Cell Biol. 5: 221-229.
37. Schmidt, J. J., and K. A. Bostian. 1997. Endoproteinase activity of type A botulinum neurotoxin: substrate requirements and activation by serum albumin. J. Protein Chem. 16: 19-26.
38. Schmidt, J. J., R. G. Stafford, and K. A. Bostian. 1998. Type A botulinum neurotoxin proteolytic activity: development of competitive inhibitors and implications for substrate specificity at the S1' binding subsite. FEBS Lett. 435: 61-64.
39. Segelke, B., M. Knapp, S. Kadkhodayan, R. Balhorn, and B. Rupp. 2004. Crystal structure of *Clostridium botulinum* neurotoxin protease in a product-bound state: evidence for noncanonical zinc protease activity. Proc. Natl. Acad. Sci. USA 101: 6888-6893.
40. Simpson, L. L., and B. R. Dasgupta. 1983. Botulinum neurotoxin type E: studies on mechanism of action and on structure-activity relationships. J. Pharmacol. Exp. Ther. 224: 135-140.
41. Simpson, L. L., J. A. Coffield, and N. Bakry. 1993. Chelation of zinc antagonizes the neuromuscular blocking properties of the seven serotypes of botulinum neurotoxin as well as tetanus toxin. J. Pharmacol. Exp. Ther. 267: 720-727.
42. Sheridan, R. E., S. S. Deshpande, J. D. Nicholson, and M. Adler. 1997. Structural features of aminoquinolines necessary for antagonist activity against botulinum neurotoxin. Toxicon 35: 1439-1451.
43. Sheridan, R. E., S. S. Deshpande, and T. Smith. 1999. Comparison of in vivo and in vitro mouse bioassays for botulinum toxin antagonists. J. Appl. Toxicol. 19: S29-S33.
44. Shone, C. C., and A. K. Roberts. 1994. Peptide substrate specificity and properties of the zinc-endopeptidase activity of botulinum type B neurotoxin. Eur. J. Biochem. 225: 263-270.
45. Silvaggi, N. R., D. Wilson, S. Tzipori, and K. N. Allen. 2008. Catalytic features of the botulinum neurotoxin A light chain revealed by high resolution structure of an inhibitory peptide complex. Biochemistry 47: 5736-5745.
46. Silvaggi, N. R., G. E. Boldt, M. S. Hixon, J. P Kennedy, S. Tzipori, K. D. Janda, and K. N. Allen. 2007. Structures of *Clostridium botulinum* neurotoxin serotype A light chain complexed with small-molecule inhibitors highlight active-site flexibility. Chemistry and Biology 14: 533-542.
47. Tang, J., J. G. Park, C. B. Millard, J. J. Schmidt, and Y. P. Pang. 2007. Computer-aided lead optimization: improved small-molecule inhibitor of the zinc endopeptidase of botulinum neurotoxin serotype A. PLoS ONE. 2(8):e761. doi:10.1371/journal.pone.0000761.
48. Voigt, J. H., B. Bienfait, S. Wang, and M. C. Nicklaus. 2001. Comparison of the NCI open database with seven large chemical structural databases. J. Chem. Inf. Comput. Sci. 41: 702-712.
49. Yowler, B. C., R. D. Kensinger, and C. L. Schengrund. 2002. Botulinum neurotoxin A activity is dependent upon the presence of specific gangliosides in neuroblastoma cells expressing synaptotagmin I. J. Biol. Chem. 277: 32815-32819.
50. Sukonpan, C. et al. 2004. Synthesis of substrates and inhibitors of botulinum neurotoxin type A metalloprotease. J. Pept. Res. 63: 181-93.

What is claimed is:

1. A composition having Formula 1

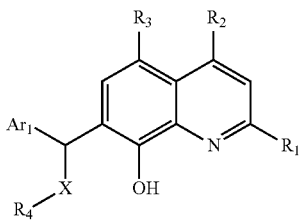

wherein $R_1$, $R_2$, and $R_3$, being the same or different, are each selected from the group consisting of a H, a $C_1$ to $C_6$ straight or branched alkyl group, an aryl group, a halogen, $NR_5R_6$, $NO_2$, $CH_2OH$, $CHO$, $CN$, $SO_3H$, and $SO_2NR_7R_8$;

wherein $R_5$, $R_6$, $R_7$, and $R_8$, being the same or different, are each selected from the group consisting of a H, a $C_1$ to $C_6$ straight or branched, or cyclic alkyl group, and an aryl group;

wherein $R_4$ is selected from the group consisting of pyridyl and quinoline; wherein when $R_4$ is a pyridyl group, at least one of $R_2$ and $R_3$ is a halogen;

wherein when $R_1$ or $R_2$ is a halogen, the halogen is selected from the group consisting of F, Cl, Br, and I;

wherein when $R_3$ is a halogen, the halogen is selected from the group consisting of F, Br, and I;

wherein $Ar_1$ is phenyl, wherein X is NH.

2. The composition of claim 1 further comprising a pharmaceutically acceptable carrier, excipient, diluent, or adjuvant.

3. The composition of claim 1 wherein the compound is a pharmaceutically acceptable salt of the compound of Formula 1.

4. A composition having Formula I

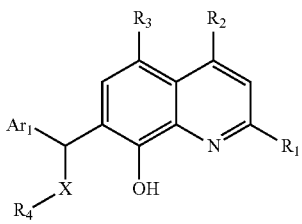

wherein $R_1$, $R_2$, and $R_3$, being the same or different, are each selected from the group consisting of a H, and a halogen;
wherein $R_4$ selected from the group consisting of a pyridyl group and a quinoline group; wherein when $R_4$ is a pyridyl group, at least one of $R_1$, $R_2$ and $R_3$ is a halogen;
wherein $Ar_1$ is phenyl;
wherein X is NH;
wherein when $R_1$ or $R_2$ is a halogen, the halogen is selected from the group consisting of F, Cl, Br, and I; and
wherein when $R_3$ is a halogen, the halogen is selected from the group consisting of F, Br, and I.

5. The composition of claim 4 further comprising a pharmaceutically acceptable carrier, excipient, diluent, or adjuvant.

6. The composition of claim 4, further wherein the compound is a pharmaceutically acceptable salt of the compound of Formula 1.

* * * * *